(12) United States Patent
Brandstädter et al.

(10) Patent No.: US 8,048,820 B2
(45) Date of Patent: Nov. 1, 2011

(54) SHAPED CATALYST BODY FOR PARTIAL OXIDATION REACTIONS

(75) Inventors: Willi Brandstädter, Holzkirchen (DE); Leopold Streifinger, Bruckmuhl (DE); Marvin Estenfelder, Karlsruhe (DE)

(73) Assignee: Sud-Chemie AG, Munich (DE)

( * ) Notice: Subject to any disclaimer, the term of this patent is extended or adjusted under 35 U.S.C. 154(b) by 547 days.

(21) Appl. No.: 12/092,012

(22) PCT Filed: Oct. 31, 2006

(86) PCT No.: PCT/EP2006/010487
§ 371 (c)(1),
(2), (4) Date: Oct. 14, 2008

(87) PCT Pub. No.: WO2007/051602
PCT Pub. Date: May 10, 2007

(65) Prior Publication Data
US 2009/0306410 A1    Dec. 10, 2009

(30) Foreign Application Priority Data

Oct. 31, 2005 (DE) .................... 10 2005 052 018
Nov. 29, 2005 (DE) .................... 10 2005 056 866

(51) Int. Cl.
*B01J 27/188* (2006.01)
*B01J 27/19* (2006.01)
*B01J 27/192* (2006.01)
*B01J 27/185* (2006.01)
*B01J 27/182* (2006.01)

(52) U.S. Cl. ........ 502/209; 502/210; 502/211; 502/212; 502/213; 502/214; 502/527.19; 502/527.24

(58) Field of Classification Search .......... 502/209–214, 502/527.19, 527.24
See application file for complete search history.

(56) References Cited

U.S. PATENT DOCUMENTS

| 5,137,860 | A | | 8/1992 | Ebner et al. |
| 5,168,090 | A | * | 12/1992 | Ebner et al. .................... 502/209 |
| 5,330,958 | A | | 7/1994 | Viola et al. |
| 5,905,054 | A | | 5/1999 | Cavalli et al. |
| 5,929,256 | A | | 7/1999 | Felthouse et al. |
| 5,939,351 | A | | 8/1999 | Rubini et al. |
| 5,945,368 | A | | 8/1999 | Felthouse et al. |
| 6,080,573 | A | | 6/2000 | Convents et al. |
| 6,166,280 | A | | 12/2000 | Rubin et al. |

(Continued)

FOREIGN PATENT DOCUMENTS

DE       100 00 584 A1    7/2001

(Continued)

*Primary Examiner* — Patricia L Hailey
(74) *Attorney, Agent, or Firm* — Millen, White, Zelano & Branigan, P.C.

(57) ABSTRACT

The invention relates to a shaped catalyst body for preparing maleic anhydride, which comprises mixed oxides of vanadium and of phosphorus as catalyst components. To develop a generic shaped catalyst body further so that it has improved properties, it is proposed that the basic geometric body enveloping the shaped catalyst body (100; 200) be a prism (180) having a first triangular face and a second triangular face and the shaped catalyst body (100; 200) be provided with three through openings (111, 121, 131; 211, 221, 231) which extend from a first face of the shaped body (100; 200) which contacts the first triangular face of the prism (180) to a second face of the shaped body (100; 200) which contacts the second triangular face of the prism (180).

27 Claims, 1 Drawing Sheet

U.S. PATENT DOCUMENTS

Figure 1:
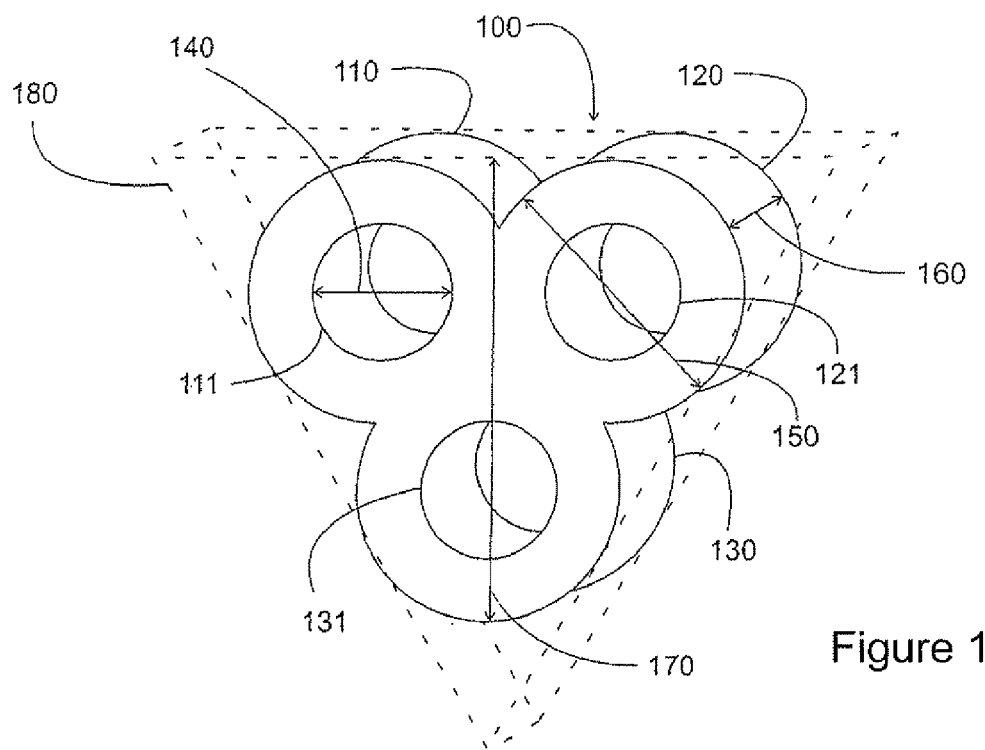

2002/0161243 A1  10/2002  Zehner et al.

FOREIGN PATENT DOCUMENTS

| EP | 0 520 972 A | 12/1992 |
| EP | 0 520 972 A1 | 12/1992 |
| EP | 0 591 572 A1 | 4/1994 |
| EP | 0 732 146 A1 | 9/1996 |
| EP | 0 775 522 A1 | 5/1997 |
| EP | 0 794 004 A1 | 9/1997 |
| EP | 1 136 120 A | 9/2001 |
| EP | 1 136 120 A1 | 9/2001 |
| WO | WO 97/12674 A1 | 4/1997 |
| WO | WO 2007/012620 A | 2/2007 |
| WO | WO 2007/012620 A1 | 2/2007 |

\* cited by examiner

SHAPED CATALYST BODY FOR PARTIAL OXIDATION REACTIONS

The present invention relates to a shaped catalyst body for the preparation of maleic anhydride, comprising mixed oxides of vanadium and of phosphorus as catalyst component.

Maleic anhydride is a chemical intermediate of considerable commercial interest. It is used, for example, in the preparation of alkyd resins and polyester resins, alone or else in combination with other acids. In addition, it is a versatile intermediate for chemical synthesis, for example for the synthesis of gamma-butyrolactone, tetrahydrofuran and 1,4-butanediol, which are in turn themselves used as solvents or processed onward to polymers, for example polytetrahydrofuran or polyvinylpyrrolidone.

Maleic anhydride is generally prepared by partial oxidation of hydrocarbons in the gas phase with molecular oxygen with a gas comprising molecular oxygen in the presence of a vanadium-phosphorus oxide catalyst (VPO). Various oxidation catalysts, various shaped catalyst bodies and various process regimes are employed. In general, the oxidation catalysts comprise mixed oxides of vanadium and phosphorus, and such oxidation catalysts comprising vanadium in a valence of from +3.8 to +4.8 have been found to be particularly suitable for the preparation of maleic anhydride from saturated hydrocarbons having at least four carbon atoms in a straight chain. As well as vanadium, phosphorus and oxygen, the VPO catalysts may also comprise promoters, for example metals, which may be present in the oxidation catalyst in the form of their oxides.

The shaped catalyst bodies used to prepare maleic anhydride by heterogeneously catalyzed gas phase oxidation of hydrocarbons, comprising vanadium, phosphorus and oxygen have various geometries.

U.S. Pat. No. 4,283,307 describes a shaped catalyst body which comprises mixed oxides of vanadium and of phosphorus for the partial oxidation of n-butane, said shaped catalyst body having a cylindrical geometry and a continuous bore passing along its longitudinal axis.

EP 1 261 424 B1 relates to a catalyst for the preparation of maleic anhydride by heterogeneously catalyzed gas phase oxidation of a hydrocarbon having at least four carbon atoms. This catalyst comprises a catalytically active material of a vanadium-phosphorus mixed oxide and has an essentially hollow cylindrical structure. The hollow cylinder has such a configuration that the ratio of the height to the diameter of the passage orifice is at most 1.5 and the ratio of the geometric surface area to the geometric volume of the shaped body is at least 2 mm$^{-1}$.

EP 0 552 287 B1 relates to a shaped catalyst body for preparing maleic anhydride, said shaped body comprising a solid geometric form having at least one void space disposed in the external surface thereof. The shaped body is formed from mixed oxides of vanadium and phosphorus and has a geometric volume of from 30% to 67% of that occupied by the solid shaped body free of void spaces, where the ratio of the geometric surface area of the shaped body to the geometric volume of the shaped body is at least 20 cm$^{-1}$.

The object of the present invention consists in providing a shaped catalyst body for preparing maleic anhydride (MA) by heterogeneously catalyzed gas phase oxidation of hydrocarbons of the type specified at the outset, which, compared to the prior art, allows the preparation of maleic anhydride with a higher selectivity and with a higher productivity, and where the end product has a lower proportion of acetic acid and acrylic acid than is the case with use of shaped bodies known to date.

This object is achieved with a shaped catalyst body of the type in question in that the fundamental geometric shape of the envelope of the shaped catalyst body is a prism having a first and a second triangular face and in that the shaped catalyst body is provided with three continuous orifices which extend from a first face of the shaped body which forms the first triangular face of the prism to a second face of the shaped body which forms the second triangular face of the prism.

Compared to the shaped catalyst bodies known in the prior art, the inventive shaped catalyst bodies are notable for an increased specific activity per g/catalyst and an increased selectivity, allowing an increased productivity of maleic anhydride and an increased maleic anhydride selectivity to be obtained by suppressing the overoxidation of maleic anhydride.

The term "Productivity" means the mass flow of MA per unit volume/reactor, expressed in the unit $$\frac{\text{kg}(MA)}{h \cdot 1_{(reactor)}}.$$

An increased productivity means that, in an existing production plant, more product, for example maleic anhydride (MA) can be synthesized per unit time.

It has also been found that, surprisingly, the product obtained with the inventive shaped catalyst body in maleic anhydride synthesis has an exceptionally low proportion of acrylic acid and acetic acid in the end product compared to existing shaped bodies; more particularly, the entirety of the two aforementioned components is 20-30% lower in accordance with the invention than when conventional shaped bodies are used.

Moreover, for a given maximum pressure loss of a catalyst bed, at least 20% higher space velocities (GHSV=volume flow/catalyst volume) can now be employed, compared to known shaped body geometries, for example spheres, solid cylindrical tablets or extrudates. When, for example, a maximum GHSV of 2500 h$^{-1}$ is possible with one of the shaped bodies known to date, space velocities of at least 3000 h$^{-1}$ are achievable using the inventive shaped bodies with the same pressure loss. Owing to the specifically lower pressure increase, it is, on the other hand, also possible to implement a given throughput, for example GHSV of 2500 h$^{-1}$, with a lower pressure loss than with conventional shaped bodies. As a result, the blower power that has to be expended is lower, leading to a saving of energy costs.

In addition, the inventive shaped catalyst bodies have a high mechanical stability, such that, for example, as the inventive shaped bodies are transported and a tube bundle reactor is filled with the inventive shaped catalyst bodies, there is essentially no damage to the shaped bodies.

In addition, it is advantageous that the inventive shaped catalyst bodies have round boundary lines. The operation of filling a reactor can thus be simpler and more reproducible, with little formation of filling gaps.

Another advantage of the inventive shaped catalyst bodies is that they have comparatively short diffusion paths. The short diffusion paths bring about a high degree of pore utilization, such that a lower catalyst mass can be used to achieve a desired hydrocarbon conversion, and they also bring about a higher MA selectivity, since the total oxidation of MA to CO and $CO_2$ is suppressed.

Prismatic-shaped catalyst bodies generally have a comparatively low stability along their longitudinal edges, such that, for example in the filling operation of a reactor with the appropriate shaped catalyst bodies, there may be flaking in the region of the longitudinal edges. In a preferred embodiment of the inventive shaped catalyst body, the shaped body has an essentially triangular cross section with rounded vertices.

In an alternative embodiment, the shaped catalyst body has an essentially trilobal cross section, each lobe being provided with a continuous orifice.

In accordance with an embodiment of the inventive shaped catalyst body which is simple to implement from a manufacturing point of view and hence inexpensive, the continuous orifices have a circular or oval cross section.

In the preparation of maleic anhydride by heterogeneously catalyzed gas phase oxidation of hydrocarbons, pressure losses occur in the reactor bed, which have an adverse effect on the gas throughput and hence on the product capacity and entail increased blower power. In order to minimize the pressure loss in the reactor and in order to achieve very short diffusion paths within the shaped catalyst body, the continuous orifices of the inventive shaped catalyst body, in a particularly preferred embodiment, have a diameter from 0.5 mm to 3 mm.

In a preferred method of manufacture, in order to positively influence the flow of the gas mixture passing through the catalyst bed in the preparation of maleic anhydride by heterogeneously catalyzed gas phase oxidation, i.e. to shorten the diffusion path with simultaneously sufficient stability, the continuous orifices may have the same diameter. In an alternative embodiment, each of the continuous orifices may have a different diameter.

In an embodiment of the shaped catalyst body which is simple in manufacturing terms and hence is particularly inexpensive, the continuous orifices run essentially parallel to one another.

It is preferred when the ratio of the intermediate spacing between the continuous orifices relative to the diameter of the orifices is from 1.15 to 1.5. This on the one hand provides a sufficient mechanical stability of the inventive shaped catalyst body and, on the other hand, such a configuration allows achievement of comparatively high space velocities of the gas mixture passing through the reactor bed.

A factor which partly determines the filling density of shaped catalyst bodies in a reactor is the geometry of the shaped catalyst bodies. In order to influence the filling density and thus to influence the space velocities of the gas passing through the catalyst bed, in a further preferred embodiment of the inventive shaped catalyst body, two of the three lobes may have the same external diameter. In an alternative embodiment, each of the lobes has a different external diameter.

Moreover, the filling density of a reactor laden with shaped catalyst bodies depends on the size of these shaped bodies. In order to obtain suitable space velocities of the gas mixture comprising hydrocarbon and oxygen in the preparation of maleic anhydride by heterogeneously catalyzed gas phase oxidation, the shaped bodies preferably have a length of from 2 to 20 mm, especially from 3 to 10 mm.

A further preference, in this connection, is that the ratio of the length of the inventive shaped body to the minimum width of the end face of the trilobal shaped body is from 0.5 to 2. The minimum width of the end face is defined by the reference numeral 170 in FIG. 1.

In the inventive shaped catalyst body, the ratio of the volume of the shaped body $V_{shaped\ body}$ to the volume of the envelope prism $V_{prism}$ is from 0.71 to 0.9. The volume of the shaped body, and also of the envelope prism, is calculated as the volume of the solid shaped body, i.e. without taking account of the continuous orifices.

The inventive shaped body usually has a geometric surface area of from 0.15 cm$^2$ to 5 cm$^2$, preferably from 0.5 cm$^2$ to 4 cm$^2$, more preferably from 1 cm to 3.5 cm$^2$, especially from 1.5 cm$^2$ to 3 cm$^2$.

In a more preferred embodiment of the inventive shaped catalyst body, the ratio of the geometric surface area of the shaped body to the volume of the shaped body is from 0.5 to 20 mm$^{-1}$, preferably from 1.4 to 4 mm$^{-1}$, and the ratio of the geometric surface area of the shaped body to its volume is especially greater than 2.1 mm$^{-1}$.

In accordance with a preferred embodiment of the inventive shaped catalyst body, the bulk density of the inventive shaped bodies is from 0.4 g/cm$^3$ to 1.4 g/cm$^3$, preferably from 0.5 g/cm$^3$ to 1.1 g/cm$^3$.

The preparation of maleic anhydride by heterogeneously catalyzed gas phase oxidation is generally carried out in "tube bundle reactors" in which shaped catalyst bodies are layered one on top of one another in vertically aligned tubes. Accordingly, a shaped catalyst body has to be able to withstand the weight of the shaped bodies on top of it. In a more preferred embodiment of the inventive shaped body, its mechanical strength is therefore from 4.0 N to 300 N, preferably from 10 N to 100 N, more preferably 15-40 N.

The BET surface area of the inventive shaped catalyst body is from 10 to 300 m$^2$/g, preferably from 15 to 80 m$^2$/g, more preferably 20-50 m$^2$/g. The BET surface area is determined by the single-point method by adsorption of nitrogen to DIN 66132.

It may also be preferred for the integral pore volume (determined to DIN 66133 (Hg porosimetry)) to be >100 mm$^3$/g, preferably >180 mm$^3$/g. In particular, it is advantageous in this context when not more than 10% of the pore volume is formed by pores of radius<10 nm and not more than 10% of the pore volume by pores of radius>500 nm.

The inventive shaped catalyst bodies may comprise the mixed oxides of vanadium and of phosphorus, for example, in pure, undiluted form as unsupported catalysts or diluted with a preferably oxidic support material as supported mixed catalysts.

Suitable support materials for the mixed catalysts are, for example, alumina, silica, aluminum silicates, zirconia, titania or mixtures thereof. The content of the catalyst component in the inventive shaped catalyst body is preferably from 3 to 50% by weight based on the total weight of the shaped catalyst body. In the case of a supported mixed catalyst, the content of the catalyst component in the inventive shaped catalyst body is 3-50% by weight, preferably 5-30% by weight, based on the total weight of the shaped catalyst body.

As well as the mixed oxides of vanadium and of phosphorus, the inventive shaped catalyst body may comprise, as a further catalytic component, a promoter which is selected from metals of the periodic table of the elements. In a preferred embodiment of the inventive shaped catalyst body, the catalyst component corresponds to the general formula $$VP_xO_yM_z$$

in which M is at least one promoter, x is from 0.1 to 3, y is a number according to the valences of V, P and M, and z is from 0 to 1.5.

As stated above, the promoter may be selected from the metals. The promoter is preferably selected from chromium, nickel, magnesium, aluminum, silicon, tungsten, niobium, antimony and/or cesium.

According to the process regime, it may be preferred to use additional promoter elements other than those mentioned above. In a corresponding process regime, it may therefore be preferred when the promoter is further selected from lithium, zinc, iron, or bismuth, tellurium, silver and/or molybdenum.

It is favorable when the proportion of the promoter in the form of an oxide or in the form of a compound which can be converted to an oxide is from 0.005% by weight to 5% by weight, based on the total weight of the shaped body.

Assistants can also be added to the inventive shaped catalyst body, for example tableting assistants or pore formers.

Tableting assistants are generally added when the inventive shaped catalyst body is shaped via tableting. Tableting assistants are generally catalytically inert and improve the tableting properties of the "catalyst precursor powder", for example by increasing the lubricity and/or free flow. A particularly suitable tableting assistant is, for example, graphite. The tableting assistants added may remain in the activated catalyst and are generally present in the shaped catalyst body in an order of magnitude of from 1 to 5% by weight, based on the total weight of the shaped catalyst body.

In addition, the inventive shaped catalyst body may comprise pore formers. Pore formers are substances which are used for controlled establishment of the pore structure in the mesopore and macropore range. They are generally compounds which contain carbon, hydrogen, oxygen and/or nitrogen, being added to the catalyst precursor powder before shaping and being decomposed or evaporated in the course of the subsequent activation of the shaped catalyst body, for example by calcination, and hence being predominantly discharged from the resultant shaped body, thus generating pores.

The invention further relates to the use of the inventive shaped catalyst body for preparing maleic anhydride from hydrocarbons.

The hydrocarbons used may be nonaromatic hydrocarbons having from 4 to 10 carbon atoms. It is necessary that the hydrocarbon contains no less than 4 carbon atoms in a straight chain or in a ring. The hydrocarbon is particularly suitably n-butane. In addition to n-butane, pentanes, hexanes, heptanes, octanes, nonanes, decanes or mixtures of any of these compounds with or without n-butane are also suitable, provided that they contain at least 4 carbon atoms in a straight chain.

Unsaturated hydrocarbons may likewise be used for conversion to maleic anhydride. Suitable unsaturated hydrocarbons are, for example, butenes (1-butene and 2-butene), 1,3-butadiene, the pentenes, the hexenes, the heptenes, the octenes, the nonenes, the decenes and mixtures of any of these compounds, with the proviso that they contain at least 4 carbon atoms in a straight chain. Equally suitable are substituted and unsubstituted furans, for example tetrahydrofuran, and also aromatic compounds, for example benzene and its derivatives.

The inventive shaped catalyst body can, for example, be produced as described in WO 97/12674, by shaping according to the inventive geometry.

The essential steps of possible production of the inventive shaped catalyst body with formation of a catalyst precursor powder, shaping and subsequent activation are explained briefly below:

Reaction of a pentavalent vanadium compound (for example $V_2O_5$) with a reducing solvent (for example isobutanol) in the presence of a pentavalent phosphorus compound (for example o-phosphoric acid or another phosphoric acid such as pyrophosphoric acids and/or mixtures thereof, etc.) and optionally of a promoter. The aforementioned reaction can optionally be carried out in the presence of a support material which is, for example, present in pulverulent form and is dispersed in the solvent.

Obtaining the resultant vanadium-, phosphorus- and oxygen-containing catalyst precursor, for example by means of filtration, evaporative concentration or centrifugation.

Drying and optionally calcining the catalyst precursor. Pulverulent support material and/or a pore former can optionally be admixed with the dried catalyst precursor. The drying can be effected, for example, under reduced pressure, under protective gas or with an excess of oxygen.

Shaping by conversion to the inventive geometry. Before the shaping, a tableting assistant can be added to the dried catalyst precursor.

Activation of the vanadium-, phosphorus- and oxygen- and optionally promoter-containing catalyst precursor by heating in an atmosphere which may comprise oxygen, nitrogen, noble gases, carbon dioxide, carbon monoxide and/or water vapor or mixtures thereof. The selection of temperature, heating rate, treatment time and gas atmosphere can determine the mechanical and/or catalytic properties of the shaped catalyst body.

The inventive shaped catalyst body can be produced, for example, by first mixing the dried catalyst precursor powder with a binder or with a lubricant. The shaped body is then produced, for example, in a tableting press with a rotary pan on whose circumference are arranged a plurality of orifices with an appropriate cross section, for example a trilobal cross section or a triangular cross section. The mixture is introduced into this orifice (dies) and is held from the bottom by a punch, by which, during the rotation of the rotary pan, for example, three pins which are at the positions of the orifices to be generated are pushed upward. In the course of further rotation of the rotary pan, a punch with an appropriate cross section engages from the top, said punch being provided with orifices into which the pins penetrate when the upper punch is pressed downward. In the course of further rotation of the rotary pan, after the lower punch has been withdrawn and the upper punch has been moved onward, the pressed shaped bodies are ejected from the dies.

The shaped catalyst body thus formed is then activated, for example by calcination.

Figure 2:
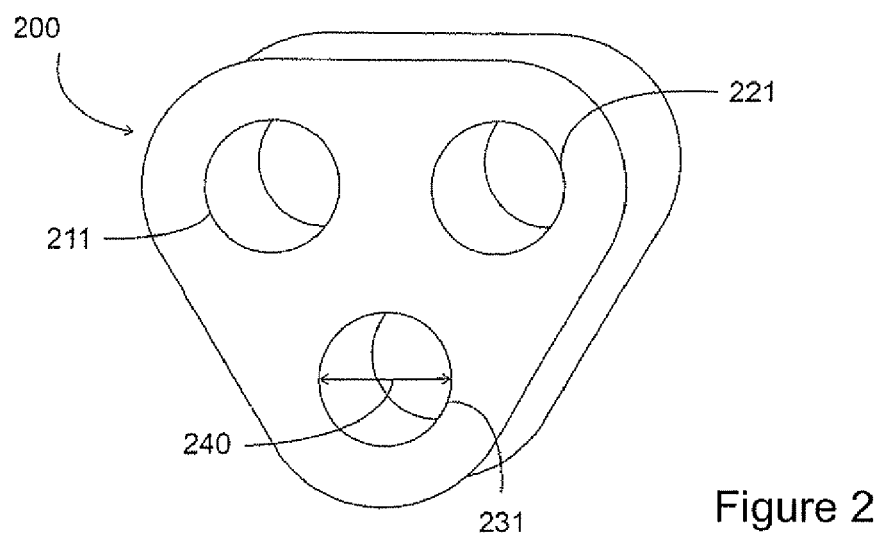

The description of two preferred embodiments of the inventive shaped catalyst body which follows serves to illustrate the invention in combination with the drawing. The drawing shows:

FIG. 1 an inventive shaped catalyst body according to a first embodiment;

FIG. 2 an inventive catalyst according to a second embodiment.

FIG. 1 shows a shaped catalyst body according to a first embodiment, which as a whole is given the reference numeral 100. The shaped catalyst body 100 is formed from mixed oxides of vanadium and of phosphorus and has a trilobal cross section. A circular orifice 111, 121, 131 passes through each of the three lobes 110, 120, 130, each of which has the same external diameter 150.

The three passage orifices 111, 121 and 131 have the same diameter 140 and are aligned parallel to one another, the longitudinal axes of the orifices 111, 121 and 131, in cross section, defining the vertices of an essentially equilateral triangle.

The ratio of the length 160 of the shaped body 100 to the minimum width of the end face 170 of the trilobal shaped body is within an order of magnitude of from 0.5 to 2.

The fundamental geometric shape of the envelope of the trilobal shaped catalyst body 100 is a prism 180.

FIG. 2 shows an inventive shaped catalyst body according to a second embodiment, which as a whole is given the reference numeral 200. The shaped body 200 has a triangular cross section with rounded vertices and is passed through by three passage bores 211, 221 and 231 aligned parallel to one another as orifices, all of which have the same diameter 240. The longitudinal axes of the passage bores 211, 221 and 231 form, in cross section, the vertices of an essentially equilateral triangle.

The invention claimed is:

1. A shaped catalyst body for preparing maleic anhydride, comprising mixed oxides of vanadium and of phosphorus as catalyst component, having a fundamental geometric shape of the envelope of the shaped catalyst body (100; 200) of a prism (180) having a first and a second triangular face, the shaped catalyst body (100; 200) being provided with continuous orifices (111, 121, 131; 211, 221, 231) which extend from a first face of the shaped body (100; 200) forming the first triangular face of the prism (180) to a second face of the shaped body (100; 200) which forms the second triangular face of the prism (180).

2. The shaped catalyst body as claimed in claim 1, wherein the shaped body (100; 200) has an essentially triangular cross section with rounded vertices.

3. The shaped catalyst body as claimed in claim 1, wherein the shaped body (100; 200) has an essentially trilobal cross section and each lobe (110, 120, 130) is provided with a continuous orifice (111, 121, 131; 211, 221, 231).

4. The shaped catalyst body as claimed in claim 3, wherein two of the three lobes (110, 120, 130) have the same external diameter (150).

5. The shaped catalyst body as claimed in claim 3, wherein all of the lobes (110, 120, 130) have a different external diameter (150).

6. The shaped catalyst body as claimed in claim 3, having a ratio of the length (160) of the shaped body (100; 200) to the minimum width of the end face (170) of the trilobal shaped body (100) of from 0.5 to 2.

7. The shaped catalyst body as claimed in claim 1, wherein the continuous orifices (111, 121, 131; 211, 221, 231) have a circular or oval cross section.

8. The shaped catalyst body as claimed in claim 1, wherein the continuous orifices (111, 121, 131; 211, 221, 231) have a diameter (140; 240) of from 0.5 mm to 3 mm.

9. The shaped catalyst body as claimed in claim 1, wherein the continuous orifices (111, 121, 131; 211, 221, 231) have the same diameter (140; 240).

10. The shaped catalyst body as claimed in claim 1, wherein each of the continuous orifices (111, 121, 131; 211, 221, 231) has a different diameter (140; 240).

11. The shaped catalyst body as claimed in claim 1, wherein the continuous orifices (111, 121, 131; 211, 221, 231) run essentially parallel to one another.

12. The shaped catalyst body as claimed in claim 1, wherein the continuous orifices (111, 121, 131; 211, 221, 231) are essentially equally spaced apart from one another.

13. The shaped catalyst body as claimed in claim 1, having a the ratio of the intermediate spacing between the continuous orifices (111, 121, 131; 211, 221, 231) to the diameter (140; 240) of the orifices (111, 121, 131; 211, 221, 231) of from 1.15 to 1.5.

14. The shaped catalyst body as claimed in claim 1, wherein the shaped body (100; 200) has a length (160) of from 2 to 20 mm.

15. The shaped catalyst body as claimed in claim 1, having a ratio of the volume of the shaped body (100; 200) $V_{shaped\ body}$ to the volume of the envelope prism (180) $V_{prism}$ of from 0.71 to 0.9.

16. The shaped catalyst body as claimed in claim 1, wherein the geometric surface area of the shaped body (100; 200) is from 0.15 cm$^2$ to 5 cm$^2$.

17. The shaped catalyst body as claimed in claim 1, having a ratio of geometric surface areas of the shaped body (100; 200) to the volume of the shaped body (100; 200) is from 0.5 to 20 mm$^{-1}$.

18. The shaped catalyst body as claimed in claim 1, having a bulk density of the shaped body of from 0.4 g/cm$^3$ to 1.4 g/cm$^3$.

19. The shaped catalyst body as claimed in claim 1, having a mechanical strength of the shaped body (100; 200) of from 4.0 N to 300 N.

20. The shaped catalyst body as claimed in claim 1, having a BET surface area of the shaped body of from 5 to 300 m$^2$/g.

21. The shaped catalyst body as claimed in claim 1, having an integral pore volume>100 mm$^3$/g.

22. The shaped catalyst body as claimed in claim 1, having a content of the catalyst component of from 3% by weight to 50% by weight, based on the total weight of the shaped catalyst body.

23. The shaped catalyst body as claimed in claim 1, wherein the catalyst component has the formula $$VP_xO_yM_z$$

in which M is at least one promoter, x is from 0.1 to 3, y is a number according to the valences of V, P and M, and z is from 0 to 1.5.

24. The shaped catalyst body as claimed in claim 23, wherein the promoter is present and is chromium, nickel, magnesium, aluminum, silicon, tungsten, niobium, antimony, lithium, zinc, tellurium, silver, iron, bismuth, molybdenum and/or cesium or mixtures thereof.

25. The shaped catalyst body as claimed in claim 23, having a proportion of the promoter in the form of an oxide or in the form of a compound convertible to an oxide of from 0.005% to 5% by weight based on the total weight of the shaped body.

26. A method for preparing maleic anhydride from hydrocarbons, comprising subjecting said hydrocarbons to partial oxidation in the presence of a catalyst according to claim 1.

27. A method as claimed in claim 26, where n-butane is used as the hydrocarbon.

* * * * *